(12) United States Patent
Mannion et al.

(10) Patent No.: US 10,080,862 B2
(45) Date of Patent: Sep. 25, 2018

(54) TUBULAR BODIES FOR MEDICAL DELIVERY DEVICES AND RELATED MANUFACTURING METHODS

(71) Applicant: Medtronic, Inc., Minneapolis, MN (US)

(72) Inventors: Madeline A Mannion, Beverly, MA (US); Kenneth C Gardeski, Plymouth, MN (US); John B Horrigan, Beverly, MA (US)

(73) Assignee: Medtronic, Inc., Minneapolis, MN (US)

( * ) Notice: Subject to any disclaimer, the term of this patent is extended or adjusted under 35 U.S.C. 154(b) by 227 days.

(21) Appl. No.: 14/885,073

(22) Filed: Oct. 16, 2015

(65) Prior Publication Data

US 2017/0043122 A1 Feb. 16, 2017

Related U.S. Application Data

(60) Provisional application No. 62/205,078, filed on Aug. 14, 2015.

(51) Int. Cl.
| | |
|---|---|
| *A61M 25/00* | (2006.01) |
| *A61F 2/95* | (2013.01) |
| *B29C 47/02* | (2006.01) |
| *B29C 47/04* | (2006.01) |
| *B29C 47/88* | (2006.01) |

(Continued)

(52) U.S. Cl.
CPC .......... *A61M 25/0012* (2013.01); *A61F 2/95* (2013.01); *A61M 25/005* (2013.01); *B29C 47/023* (2013.01); *B29C 47/04* (2013.01); *B29C 47/8805* (2013.01); *B29C 63/00* (2013.01); *B29C 63/18* (2013.01);
(Continued)

(58) Field of Classification Search
CPC ............ A61M 25/005; A61M 25/0053; A61M 25/0012; A61M 25/0054; A61M 25/0052
See application file for complete search history.

(56) References Cited

U.S. PATENT DOCUMENTS

| | | |
|---|---|---|
| 4,630,611 A | 12/1986 | King |
| 4,915,490 A | 4/1990 | Ramsay et al. |

(Continued)

FOREIGN PATENT DOCUMENTS

WO    2015164280 A1    10/2015

OTHER PUBLICATIONS

K80-72 Series Fine Wire Braiders Machine Installation & Set-Up, Aug. 12, 2005, 19 pages, Steeger USA.

*Primary Examiner* — Kami A Bosworth
*Assistant Examiner* — William Carpenter

(57) ABSTRACT

A tubular wall, which may be employed in a medical catheter or medical electrical lead, is formed by stranding together a plurality of polymer fibers and at least one metal filar, wherein the stranding forms a braid matrix of the polymer fibers and a coil of the metal filar interlaced therewith. Then, while the braid matrix secures a pitch of the coil, a polymer material is extruded around an entire length of the tubular wall, and, in some cases, the extrusion process causes the plurality of polymer fibers to melt and coalesce together with one another, while the pitch of the coil is maintained. Alternately, a reflow process, which follows extrusion, causes the polymer fibers to melt and coalesce along all, or just a discrete length of the tubular wall.

14 Claims, 5 Drawing Sheets

(51) Int. Cl.
  B29C 63/00 (2006.01)
  B29C 63/18 (2006.01)
  B29C 47/00 (2006.01)
  B29C 63/24 (2006.01)

(52) U.S. Cl.
  CPC ...... *A61M 25/0045* (2013.01); *B29C 47/0023* (2013.01); *B29C 63/0069* (2013.01); *B29C 63/24* (2013.01)

(56) References Cited

U.S. PATENT DOCUMENTS

| | | |
|---|---|---|
| 5,019,057 A | 5/1991 | Truckai |
| 5,279,596 A * | 1/1994 | Castaneda ........... A61M 25/005 138/133 |
| 5,462,523 A | 10/1995 | Samson et al. |
| 5,674,272 A | 10/1997 | Bush et al. |
| 5,702,373 A | 12/1997 | Samson |
| 5,957,974 A | 9/1999 | Thompson et al. |
| 6,171,295 B1 | 1/2001 | Garabedian et al. |
| 6,212,995 B1 | 4/2001 | Hasegawa et al. |
| 6,213,995 B1 | 4/2001 | Steen et al. |
| 6,939,337 B2 | 9/2005 | Parker et al. |
| 7,108,716 B2 | 9/2006 | Burnside et al. |
| 7,130,700 B2 | 10/2006 | Gardeski et al. |
| 7,807,925 B2 | 10/2010 | Zarembo |
| 7,815,975 B2 | 10/2010 | Pursley |
| 8,377,035 B2 | 2/2013 | Zhou et al. |
| 8,515,556 B2 | 8/2013 | Ries et al. |
| 8,529,719 B2 | 9/2013 | Pingleton et al. |
| 8,752,591 B2 | 6/2014 | Montalvo et al. |
| 8,821,510 B2 | 9/2014 | Parker |
| 8,926,588 B2 * | 1/2015 | Berthiaume ............ A61F 2/966 604/528 |
| 2003/0028173 A1 * | 2/2003 | Forsberg ........... A61M 25/0045 604/527 |
| 2006/0030835 A1 | 2/2006 | Sherman et al. |
| 2011/0218602 A1 | 9/2011 | Kampa et al. |
| 2013/0103047 A1 * | 4/2013 | Steingisser .......... A61N 1/3756 606/129 |
| 2015/0305807 A1 | 10/2015 | Kelly et al. |

* cited by examiner

TUBULAR BODIES FOR MEDICAL DELIVERY DEVICES AND RELATED MANUFACTURING METHODS

CROSS-REFERENCE TO RELATED APPLICATIONS

This application claims the benefit of U.S. Provisional Application No. 62/205,078, filed on Aug. 14, 2015. The disclosure of the above application is incorporated herein by reference in its entirety.

TECHNICAL FIELD

The present invention pertains to medical delivery devices, and more particularly to related constructions and improved manufacturing methods for tubular bodies thereof.

BACKGROUND

Tubular bodies for medical delivery devices, such as medical . electrical leads and guiding, or delivery catheters, may have specialized structural features lending to the function of the devices. A variety of constructions for these bodies are known to those skilled in the art. However, there is a need for new tubular body constructions, which are formed by more efficient manufacturing methods.

SUMMARY

Various methods of manufacturing for elongate tubular bodies employed by medical delivery devices are disclosed herein, along with associated embodiments of device bodies.

According to some methods, a tubular wall is formed by stranding together a plurality of elongate strands, wherein the plurality of strands include a plurality of polymer fibers and at least one metal filar, and the stranding forms a braid matrix of the plurality of polymer fibers and a coil of the at least one metal filar, the coil being interlaced with the braid matrix. Then, while the braid matrix of the plurality of polymer fibers secures a pitch of the coil along a length of the coil, a polymer material is extruded around an entire length of the tubular wall, wherein, according to some methods, the extrusion process heats the tubular wall, for a sufficient period of time, to a temperature that causes the plurality of polymer fibers to melt and coalesce together with one another, while the pitch of the coil is maintained. According to some alternate methods, a reflow process that follows the extrusion process, causes the plurality of polymer fibers melt and coalesce together with one another along all or just a discrete length of the tubular wall.

A length of a tubular body of a medical catheter, according to some embodiments, includes a melted length of a braid matrix of a plurality of polymer fibers, a length of a coiled metal filar embedded in the melted length of the braid matrix, having been formed together with the braid matrix by a stranding process, and an extruded polymer material overlaying the braid matrix and coiled metal filar. In some embodiments, another, distal-most length of the catheter body defines a receptacle for an implantable medical device, the distal-most length being terminated by an opening into the receptacle, and the opening being sized to allow passage of the medical device therethrough.

A tubular body of a medical electrical lead, according to some additional embodiments, includes a tubular insulation layer, which is defined by a braid matrix of a plurality of polymer fibers overlaid with an extruded polymer material, and a conductor coil, having been formed together with the braid matrix of polymer fibers by a stranding process that interlaced the coil with the braid matrix; wherein the conductor coil is electrically isolated by the insulation layer and a length of the conductor coil is embedded in a melted length of the braid matrix. In some embodiments, a plurality of filars defines the conductor coil, and each filar may include a conductive core surrounded by an insulative jacket.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
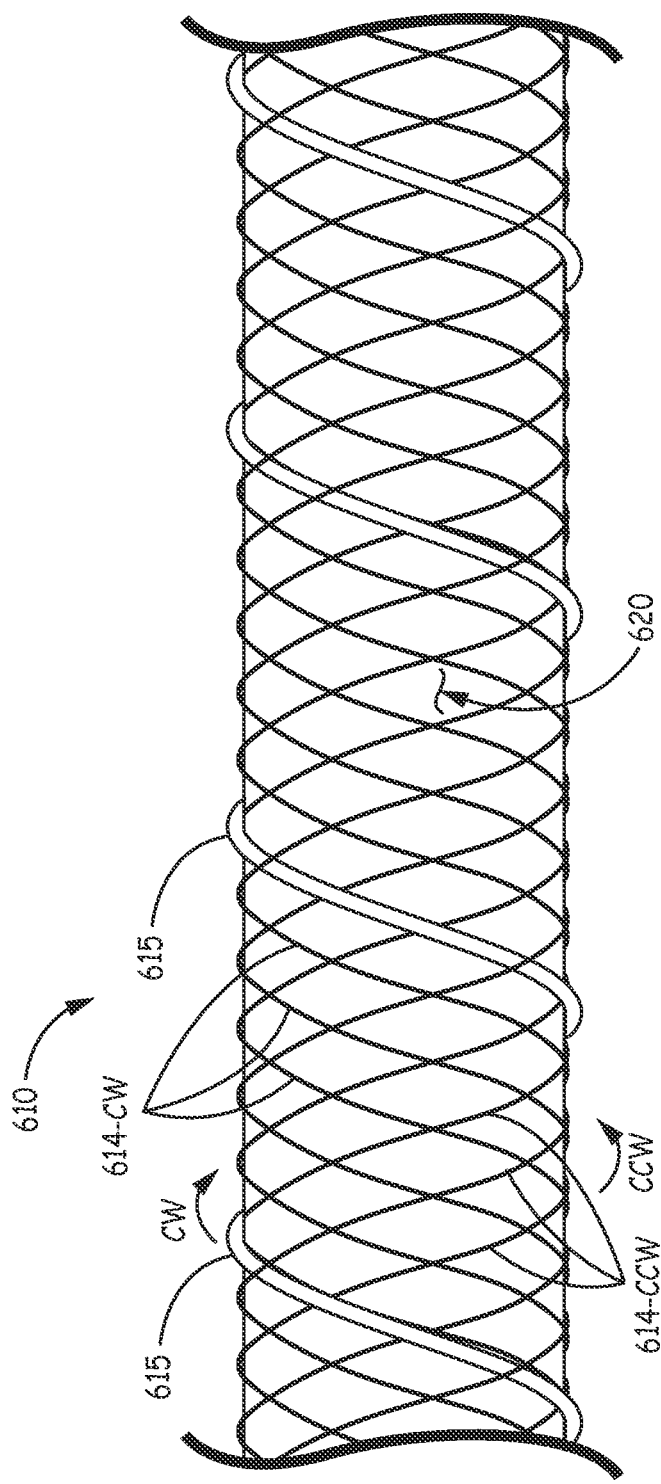
FIG. 1 is a plan view of a portion of a tubular wall formed according to some methods of the present invention.
Figure 2:
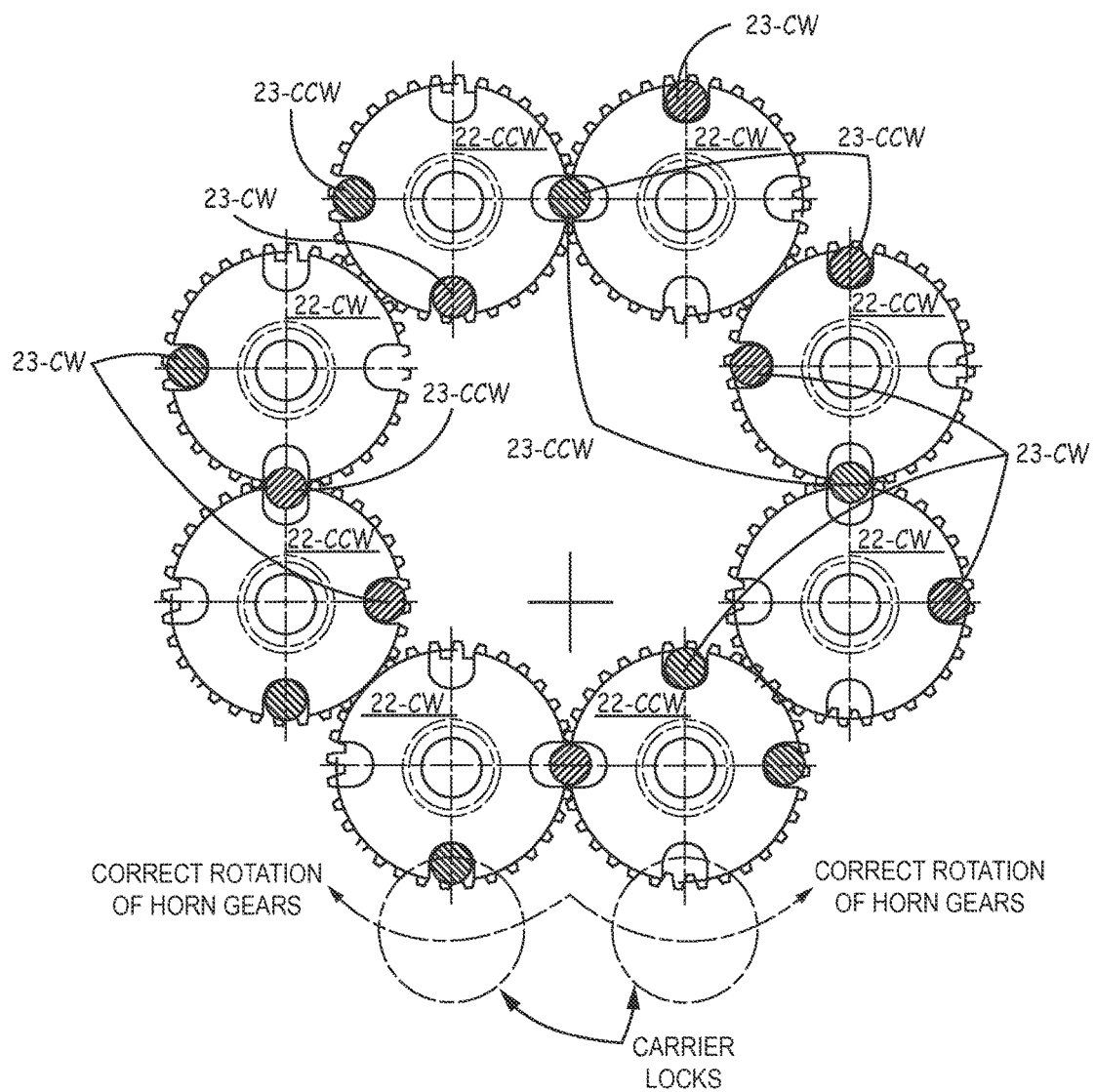
FIG. 2 is a plan view of a portion of an exemplary planetary stranding machine representative of that which may be employed to manufacture the tubular wall of FIG. 1, according to some methods.

FIG. 1 is a plan view of a portion of a tubular wall 610 formed according to some methods of the present invention; and FIG. 2 is a plan view of a portion of an exemplary planetary stranding machine representative of that which may be employed to manufacture at least a portion of tubular wall 610, according to some methods. FIG. 1 illustrates a plurality of elongate strands that include a braid matrix of a plurality of polymer fibers 614 (-CW or -CCW) and a coil of at least one metal filar 615, all of which have been stranded together to form at least a portion of tubular wall 610, wherein polymer fibers 614-CW and the at least one metal filar 615 wrap in a clockwise direction, polymer fibers 614-CCW wrap in a counter-clockwise direction, and the coil is interlaced with the braid matrix. With reference to FIG. 2, which is adapted from a diagram in a Steeger usa K80-72 series Fine Wire Braiders instruction manual, each fiber 614-CW and each of the at least one metal filar 615 may be drawn from a corresponding bobbin 23-CW that is loaded onto a corresponding horn gear 22-CW or 22-CCW, and each fiber 614-CCW may be drawn from a corresponding bobbin 23-CCW also loaded onto a corresponding horn gear 22-CW or 22-CCW. The counter-rotating horn gears 22-CW, 22-CCW drive bobbins 23-CW in a clockwise direction, and bobbins 23-CCW in a counter-clockwise direction, around a core that moves linearly (out from the page) within a perimeter of horn gears and through a braid cone of the stranding machine (not shown), to create a tubular braid matrix, for example, tubular wall 610 of FIG. 1. The core may include a polymer tube, supported by a mandrel, wherein the polymer tube forms an optional polymer liner 620 extending within tubular wall 610, as shown in FIG. 1. Those skilled in art are familiar with the construction of various types of stranding machines that are suitable for forming tubular wall 610, with or without liner 620, so further detailed description is not provided herein. Likewise, those skilled in the art are familiar with extrusion processes and associated equipment which may be employed to manufacture optional liner 620.

According to methods of the present invention, a polymer material is extruded around tubular wall 610, with or without liner 620 extending therein, while the braid matrix of polymer fibers 614 secures a pitch of the coil, formed from the at least one metal filar 615, along an entire length of wall 610. According to some methods, during the extrusion of the polymer, tubular wall 610 is heated, for a sufficient period of time, to a temperature that causes polymer fibers 614 to melt and coalesce together while the pitch of the coil is maintained. In these methods the extruded polymer material and the polymer fibers may be of the same material or of materials having generally the same melt temperature. According to some alternate methods, the temperature at which polymer fibers 614 melt and coalesce is not reached for a sufficient time during the extrusion process, so these methods include a subsequent step in which, by a reflow process, the temperature is held for a sufficient period of time to cause polymer fibers 614 to melt and coalesce along all or a portion of a length of the tubular wall. In an exemplary reflow process, tubular wall 610 is mounted on a tooling mandrel and then inserted within a sacrificial tubing of a heat shrink material (e.g., a fluoropolymer such as FEP or PTFE), which is then heat-shrunk around tubular wall 610 and held at a temperature above the melt temperature(s) of the extruded material and the polymer fiber material, for example, in an oven or a vertical fuser, for a sufficient time to melt and coalesce the materials together while the pitch of the coil is maintained. Exemplary materials suitable for the extruded material and for polymer fibers 614, in conjunction with corresponding melt temperatures, for various embodiments, are presented below.

The above-described methods are useful for increasing an efficiency in manufacturing tubular bodies for medical delivery devices, for example, catheters and electrical leads, constructions of which, according to some embodiments, are described in conjunction with FIGS. 3A-4B. For example, rather than separately manufacturing and then assembling together an extruded polymer wall and a coil of at least one metal filar, each having particular properties lending to a desired flexibility of the resulting tubular body, the above-described methods allow for the integration of assembly steps into an automated high-volume production line.

Figure 3A:
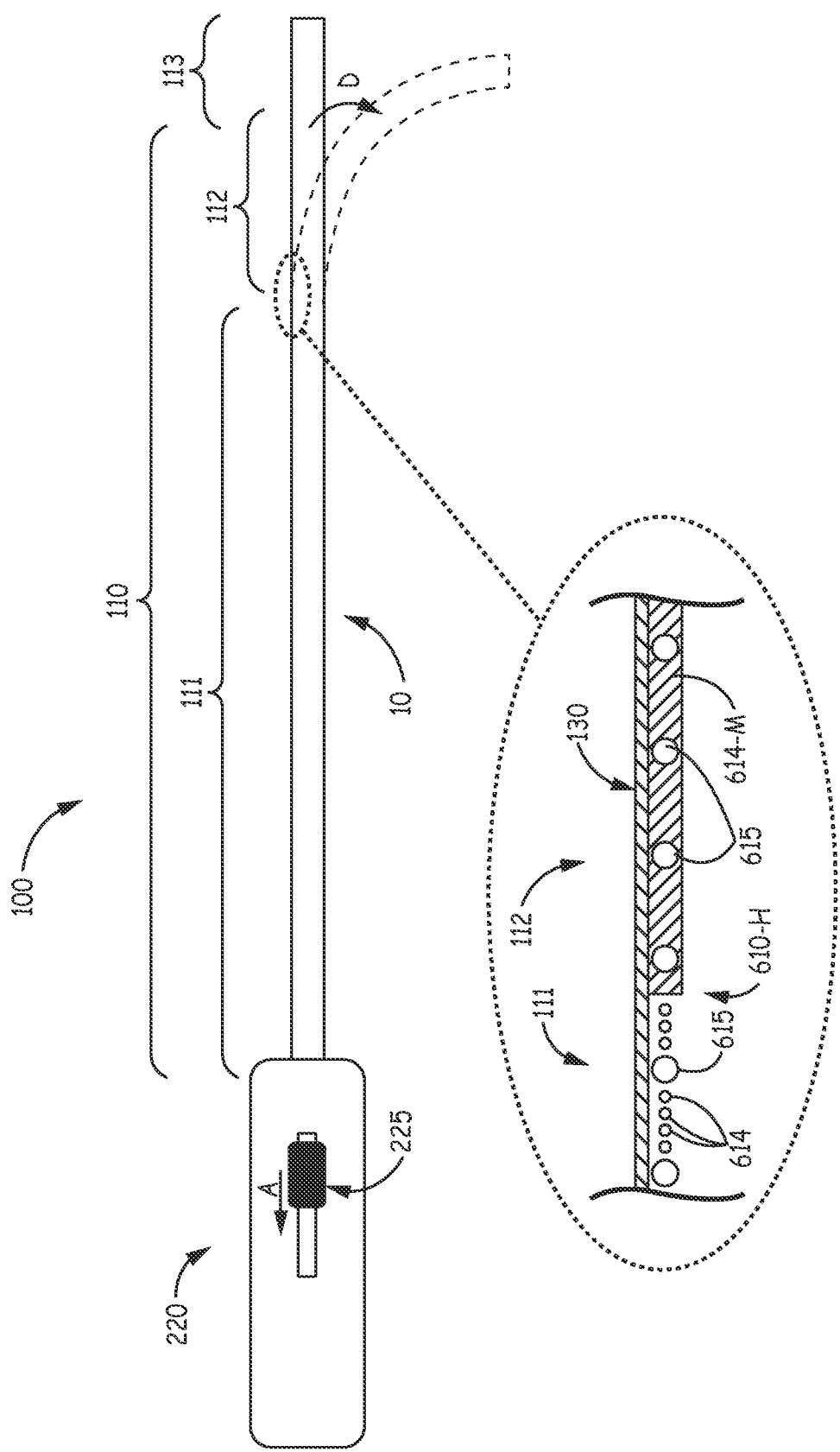
FIG. 3A is a plan view of an exemplary medical catheter, with detailed cross-section view of a portion of a tubular body of the catheter, according to some embodiments.

FIG. 3A is a plan view of an exemplary medical catheter 100, with a detailed cross-section view of a portion of a tubular body 10 thereof, according to some embodiments. FIG. 3A illustrates body 10 coupled to a handle 220, divided into a proximal length 110 and a distal-most length 113, and including a tubular wall 610-H and an overlaying extruded polymer layer 130, each of which extends along an entirety of proximal length 110. Proximal length 110 is shown including a proximal segment 111 and a distal, more flexible segment 112, for example, being deflectable, per arrow D, by a pull wire (not shown) that may be activated by moving a control member 225 of handle 220 per arrow A. FIG. 3A further illustrates tubular wall 610-H including the braid matrix of plurality of polymer fibers 614 and the at least one coiled metal filar 615, having been interlaced therewith, for example, as described above in conjunction with FIGS. 1-2, wherein a melted length 614-M of the braid matrix, in which metal filar 615 is embedded, extends only along distal segment 112.

According to the illustrated embodiment, the extrusion of polymer layer 130 around braid matrix of polymer fibers 614 and coiled metal filar 615 did not melt and coalesce fibers 614, thus a reflow process, for example, as described above, was employed following the extrusion process to melt and coalesce fibers along distal segment 112. According to some embodiments distal-most length 113 may be defined by an extension of polymer layer 130 and tubular wall 610-H, in which fibers 614 may or may not be melted and coalesced together, and which may include a radiopaque marker band incorporated therein. Alternately, distal-most length 113 may be independently formed apart from proximal length 110 and subsequently bonded thereto by any suitable means known in the art. An outer diameter of tubular body 10 of catheter 100 may be approximately isodiametric along an entire length thereof in some embodiments, for example, being between 7F (0.09 inch) and 25F (0.325 inch). According to an exemplary embodiment, coiled metal filar 615 is formed from stainless steel, polymer fibers 614 are formed from a relatively high durometer medical grade polyether block amide (e.g. a 72D PEBAX®, such as Arkema PEBAX® 7233 SA-01), and extruded polymer layer 130 from a lower durometer PEBAX® (e.g., in the range of 35D to 55D), wherein an extrusion temperature may be between 190° C. and 210° C., and a subsequent reflow process may hold tubular wall 610-H a temperature around 220° C. for six to ten minutes. According to another exemplary embodiment, polymer fibers 614 are formed from a medical grade polyethylene terephthalate (PET, either monofilament or multi-filar yarn with a melt temperature of 260° C.) and extruded polymer layer 130 from a medical grade nylon, such as an appropriate grade of the thermoplastic polyamide GrilamidO, which may be extruded at a temperature of approximately 248° C.

Figure 3B:
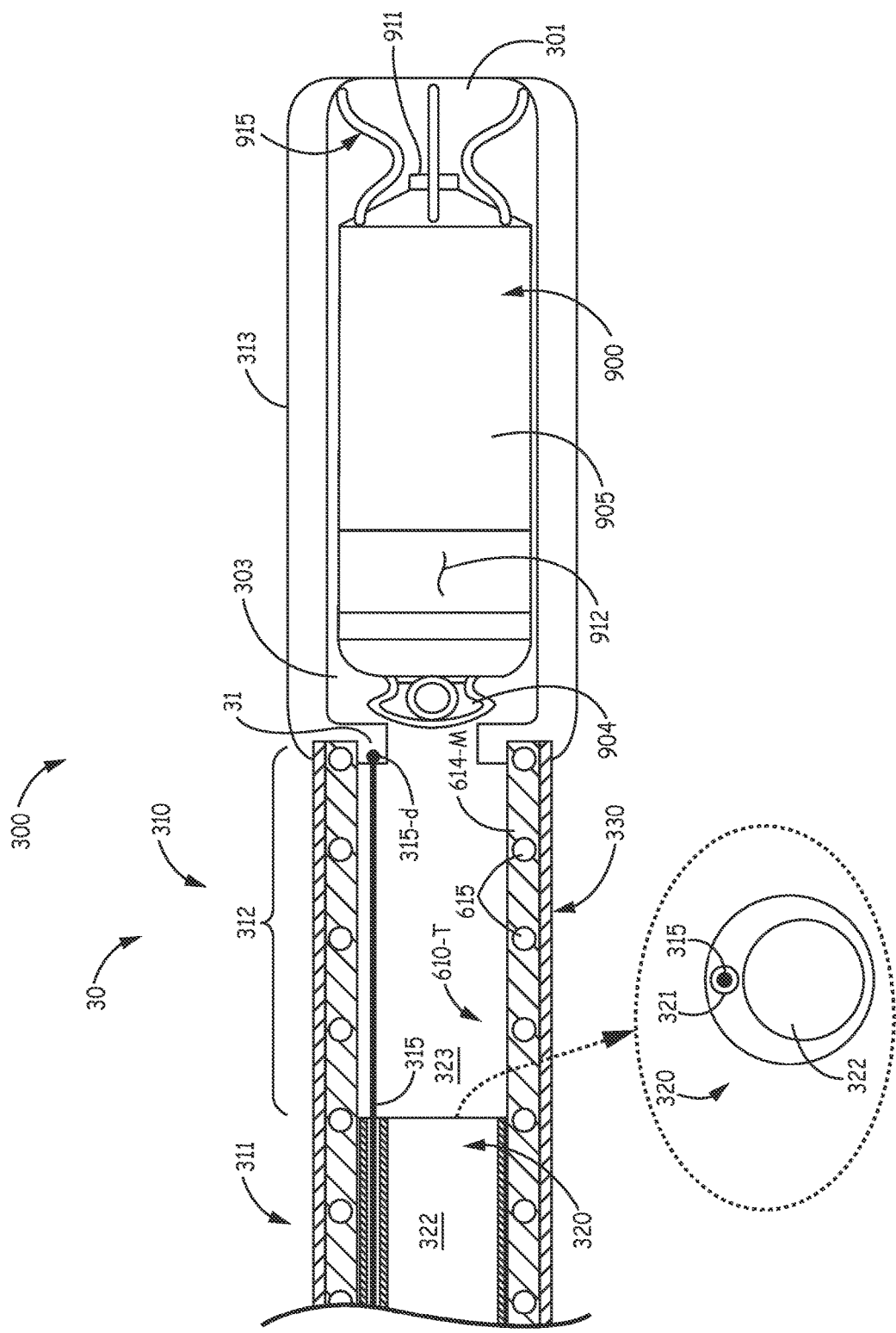
FIG. 3B is a longitudinal cross-section view of a distal portion of a tubular body of a medical catheter, with an axial cross-section view of a liner of the tubular body, according to some alternate embodiments.

FIG. 3B is a longitudinal cross-section view of a distal portion of a tubular body 30 of a medical catheter 300, according to some alternate embodiments, wherein body 30, like body 10 of catheter 100 is divided into a proximal length 310 and a distal-most length 313, but wherein body 30 further includes a multi-lumen polymer liner 320, an axial cross-section view of which is shown. FIG. 3B illustrates liner 320 extending within a proximal segment 311 of proximal length 310, and tubular body 30 further including a tubular wall 610-T and an overlaying polymer layer 330. Although not shown, catheter 300 may further include a handle similar to handle 220 of catheter 100, which is coupled to a proximal end of proximal length 310 of tubular body 30, and wherein polymer layer 330, tubular wall 610-T, and liner 320 all extend proximally into close proximity with the proximal end of proximal length 310. FIG. 3B further illustrates proximal length 310 including a distal segment 312 that extends distally from proximal segment 311 and being more flexible, due to the termination of liner 320, for deflection via a pull wire 315, for example, in a manner similar to that described above for catheter 100. Pull wire 315 is shown extending within a lumen 321 of liner 320 and distally therefrom to a distal end 315-d thereof, which is coupled to an internal shoulder 31 of distal-most length 313, for example, by mechanical interlocking therewith.

According to the illustrated embodiment, tubular wall 610-T, including the plurality of polymer fibers 614 and the at least one metal filar 615, was initially formed around liner 320, for example, as described above in conjunction with FIGS. 1-2, and the subsequent extrusion of polymer layer 330 caused fibers 614 to melt and coalesce along an entirety of proximal length 310 so that an entire length of tubular wall 610-T includes the melted and coalesced braid matrix of polymer fibers 614-M with coiled metal filar 615 embedded therein, the pitch of which was maintained by the matrix of polymer fibers 614 during the extrusion of polymer layer 330. According to an exemplary embodiment, both polymer fibers 614 and polymer layer 615 are formed from a medical grade polyether block amide PEBAX®, or a nylon, such as VESTAMID®, and liner 320 is formed, for example, by extrusion, from a medical grade High Density Polyethylene (HDPE) or PEBAX®. In another exemplary embodiment, polymer fibers 614 may be formed from PET (either monofilament or multi-filar yarn with a melt temperature of 260° C.) and polymer layer 615 from TROGAMID® (with a melt temperature around 280° C.).

With further reference to FIG. 3B, distal-most length 313 of tubular body 30 is shown defining a receptacle 303 for an implantable medical device 900, wherein distal-most length 313 is terminated by a distal opening 301 into receptacle 303, which is sized to allow passage of device 303 therethrough. Device 900 is shown including an hermetically sealed enclosure 905, which contains an electronic controller and associated power source (not shown) within a relatively compact form factor, an electrode 911 coupled to the contained controller via an hermetically sealed feedthrough assembly known in the art, and a fixation member 915 mounted around electrode 911. Enclosure 905 may be overlaid with an insulative layer, for example, medical grade polyurethane, parylene, or silicone, and a portion of the insulation layer may be removed to form another electrode 912, for example, to provide bipolar pacing and sensing in conjunction with electrode 911, when device 900 is deployed out through opening 301 and fixation member 915 secures electrode 911 in intimate tissue contact at a target implant site. FIG. 3B further illustrates device 900 including an attachment member 904 configured for coupling with a tether, and/or a deployment tool, and/or a snare tool, each of which may extend within lumens 322, 323 of tubular body 30. According to an exemplary embodiment, distal-most length 313, for example, formed from a medical grade polyether block amide (e.g., PEBAX® 7233 SA-01) or stainless steel, has an outer diameter of approximately 0.3 inch (7.6 mm), and receptacle 303 has a diameter of approximately 0.27 inch (7 mm) that extends over a length of approximately 1.3 inches (33 mm) from a location just distal to internal shoulder 31 to distal opening 301.

Figure 4A:
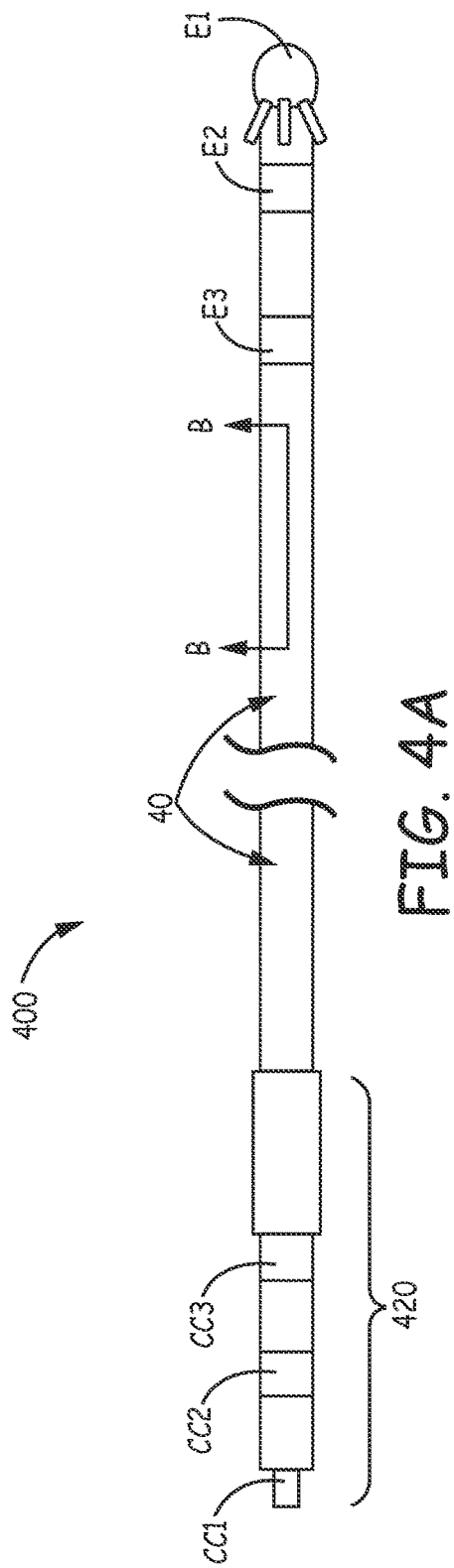
FIG. 4A is a plan view of an exemplary medical electrical lead, according to some embodiments.
Figure 4B:
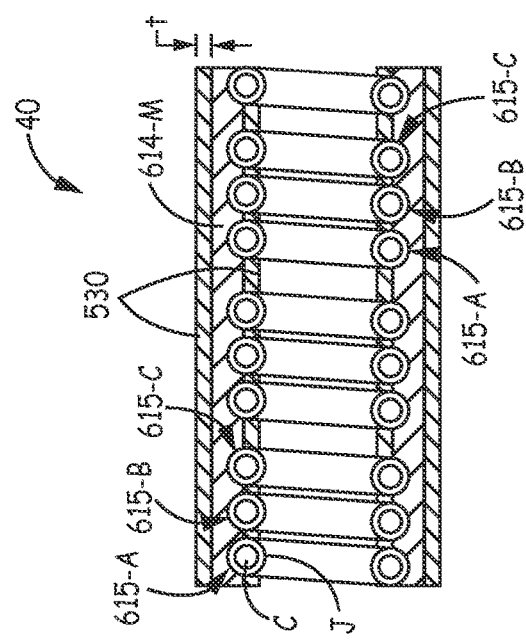
FIG. 4B is a cross-section view, per section line B-B of FIG. 4A, according to some embodiments.

FIG. 4A is a plan view of an exemplary medical electrical lead 400, according to some embodiments; and FIG. 4B is a cross-section view, per section line B-B of FIG. 4A, according to some embodiments. FIG. 4A illustrates lead 400 including an elongate tubular body 40 coupled to a connector terminal 420, a tip electrode E1 coupled to a distal end of body 40, and two more electrodes E2, E3 mounted around body 40, for example, in proximity to the distal end thereof. Each electrode E1, E2, E3 may be electrically coupled to a corresponding connector terminal contact CC1, CC2, CC3 by a corresponding filar 615-A, 615-B, 615-C of a conductor coil of tubular body 40, which can be seen in FIG. 4B. A tubular insulation layer of tubular body 40 is shown including an extruded polymer material 530 overlaying and infusing through the melted and coalesced braid matrix of polymer fibers 614-M, wherein the conductor coil, having been formed together with the braid matrix of polymer fibers 614, for example, by the stranding process described above in conjunction with FIGS. 1-2, is electrically isolated by the insulation layer. FIG. 4B further illustrates each filar 615-A, 615-B, 615-C including a conductive core C, for example, formed from a medical grade metal alloy such as MP35N and having a diameter of approximately 0.004 inch, surrounded by an insulative jacket J, for example, a medical grade fluoropolymer such as Ethylene Tetrafluoroethylene (ETFE), or a solution-imidized polyimide, having a thickness in the range of 0.0005 inch to 0.003 inch. According to the illustrated embodiment, a pitch of an entire length of the coiled filars 615-A, 615-B, 615-C was held in place by the braid matrix of polymer fibers 614 during the extrusion of polymer material 530, and became embedded in the melted braid matrix 614-M during the extrusion process.

Polymer fibers 614 and extruded polymer material 530 employed by body 40 may each be formed from a medical grade polyurethane such as Elasthane™ having a 55D durometer. In some alternate embodiments, fibers 614 are formed from 75D durometer Elasthane™, or from a mix of the 55D and 75D grades, wherein the portion of fibers 614 formed from the 55D material may be selectively melted into extruded polymer material 530. In any case, an initial rectangular cross-section of fibers 614 is preferred, for example, 0.001 inch×0.012 inch, or narrower, at 0.001 inch×0.006 inch, to control melt-through. According to an exemplary embodiment, tubular body 40 may have a maximum outer diameter of approximately 0.031 inch and a nominal inner diameter of approximately 0.019 inch; and a maximum overall thickness of the tubular insulation layer is approximately 0.0045 inch, while a minimum overlaying thickness t of extruded polymer material 530 is approximately 0.001 inch. Those skilled in the art are familiar with lead construction methods that may be employed to electrically couple each filar 615-A, 615-B, 615-C to the corresponding electrode E1, E2, E3, and to the corresponding connector terminal contact CC1, CC2, CC3.

In the foregoing detailed description, the invention has been described with reference to specific embodiments. However, it may be appreciated that various modifications and changes can be made without departing from the scope of the invention as set forth in the appended claims.

For example, the following Items are illustrative of further embodiments:

Item 1. A method for manufacturing an elongate tubular body for a medical delivery device, the method comprising:
  stranding together a plurality of elongate strands to form a tubular wall, the plurality of strands comprising a plurality of polymer fibers and at least one metal filar, and the stranding forming a braid matrix of the plurality of polymer fibers and a coil of the at least one metal filar, the coil being interlaced with the braid matrix;
  extruding a polymer material around an entire length of the tubular wall, while the braid matrix of the plurality of polymer fibers secures a pitch of the coil along a length of the coil; and
  heating the tubular wall to a temperature that causes the plurality of polymer fibers to melt and coalesce together with one another, while the pitch of the coil is maintained.

Item 2. The method of item 1, wherein heating the tubular wall to the temperature coincides with extruding the polymer material.

Item 3. The method of any one of items 1-2, wherein heating the tubular wall to the temperature comprises heating only a discrete length of the tubular wall by a re-flow process.

Item 4. The method of any one of items 1-3, wherein heating the tubular wall follows extruding the polymer material.

Item 5. The method of any one of items 1-4, further comprising extruding a polymer liner prior to stranding; and wherein the stranding forms the tubular wall around the polymer liner.

Item 6. The method of any one of items 1-5, wherein the at least one metal filar comprises a plurality of metal filars.

Item 7. The method of any one of items 1-6, wherein the plurality of polymer fibers and the extruded polymer material comprise the same material.

Item 8. An elongate tubular body for a medical catheter, the body having a proximal length and a distal-most length, and the body comprising:
  a tubular wall extending along an entirety of the proximal length of the tubular body, the tubular wall comprising a braid matrix of only a plurality of polymer fibers, and at least one metal filar formed in a single coil, the coil having been formed together with the braid matrix of polymer fibers by a stranding process that interlaced the coil with the braid matrix, a length of the braid matrix being melted such that the plurality of polymer fibers are coalesced together along the length, and a length of the coil being embedded in the melted braid matrix; and
  an extruded polymer layer overlaying the tubular wall.

Item 9. The body of item 8, wherein the melted length of the braid matrix and the corresponding embedded length of the coil extend only along a distal segment of the proximal length, the distal segment extending adjacent to the distal-most length.

Item 10. The body of any one of items 8-9, further comprising a polymer liner extending along all or a portion of the proximal length, the braid matrix and coil extending around the liner, and the proximal segment extending proximally from the distal segment.

Item 11. The body of any one of items 8-10, wherein the polymer liner extends only along a proximal segment of the proximal length, and the polymer liner comprises a multi-lumen tube.

Item 12. The body of any one of items 8-11, wherein the distal-most length includes an internal shoulder, and a distal end of the coil extends around the shoulder; and the liner includes a lumen to accommodate a pull wire of the catheter so that a distal end of the pull wire can be coupled to the shoulder of the distal-most length.

Item 13. The body of any one of items 8-12, wherein the distal-most length defines a receptacle for an implantable medical device, the distal-most length being terminated by an opening into the receptacle, the opening being sized to allow passage of the medical device therethrough.

Item 14. The body of any one of items 8-13, wherein the distal-most length defines a receptacle for an implantable medical device, the distal-most length being terminated by an opening into the receptacle, the opening being sized to allow passage of the medical device therethrough.

Item 15. An elongate tubular body for a medical electrical lead comprising:
  a tubular insulation layer extending along an entire length of the tubular body, the insulation layer comprising a braid matrix of a plurality of polymer fibers and an extruded polymer material overlaying and infusing through the braid matrix, a length of the braid matrix being melted such that all or a portion of the plurality of polymer fibers are coalesced together along the length; and
  a conductor coil extending along the entire length of the tubular body, the coil being electrically isolated by the insulation layer, the coil having been formed together with the braid matrix of polymer fibers by a stranding process that interlaced the coil with the braid matrix, and a length of the conductor coil being embedded in the melted braid matrix.

Item 16. The body of item 15, wherein the melted length of the braid matrix extends along the entire length of the body.

Item 17. The body of any one of items 15-16, wherein the conductor coil comprises a plurality of filars.

Item 18. The body of any one of items 15-17, wherein each filar of the plurality of filars comprises a conductive core surrounded by an insulative jacket.

Item 19. The body of any one of items 15-18, wherein the plurality of polymer fibers and the extruded polymer material comprise the same material, the material being a medical grade polyurethane.

Item 20. The body of any one of items 15-19, wherein the plurality of polymer fibers comprise two portions, a first of the two portions being a 55D durometer medical grade polyurethane, and a second of the two portions being a 75D durometer medical grade polyurethane.

The invention claimed is:

1. A method for manufacturing an elongate tubular body for a medical delivery device, the body having a proximal length and a distal-most length, the method comprising:
  stranding together a plurality of elongate strands to form a tubular wall extending along an entirety of the proximal length of the tubular body, the plurality of strands comprising a plurality of polymer fibers and at least one metal filar, and the stranding forming a braid matrix of the plurality of polymer fibers and a coil of the at least one metal filar, the coil being interlaced with the braid matrix, the at least one metal filar defining a first cross-sectional area and each polymer fiber of the plurality of polymer fibers defining a second cross sectional area that is smaller than the first cross-sectional area;
  extruding a polymer material around an entire length of the tubular wall, while the braid matrix of the plurality of polymer fibers secures a pitch of the coil along a length of the coil;
  heating only a discrete length of the tubular wall to a temperature that causes the plurality of polymer fibers to melt and coalesce together with one another while the pitch of the coil is maintained; and
  wherein the proximal length includes a proximal segment and a distal segment, wherein the melted length of the braid matrix extends only along the distal segment of the proximal length.

2. The method of claim 1, wherein heating the tubular wall to the temperature coincides with extruding the polymer material.

3. The method of claim 1, wherein heating the tubular wall to the temperature comprises heating only the discrete length of the tubular wall by a re-flow process.

4. The method of claim 3, wherein heating the tubular wall follows extruding the polymer material.

5. The method of claim 1, further comprising extruding a polymer liner prior to stranding; and wherein the stranding forms the tubular wall around the polymer liner.

6. The method of claim 1, wherein the at least one metal filar comprises a plurality of metal filars.

7. The method of claim 1, wherein the plurality of polymer fibers and the extruded polymer material comprise the same material.

8. An elongate tubular body for a medical catheter, the body having a proximal length and a distal-most length, and the body comprising:

a tubular wall extending along an entirety of the proximal length of the tubular body, the tubular wall comprising a braid matrix of a plurality of polymer fibers and a coil that includes at least one metal filar, the metal filar defining a first cross-sectional area and each polymer fiber of the plurality of polymer fibers defining a second cross sectional area that is smaller than the first cross-sectional area, the coil having been formed together with the braid matrix of polymer fibers by a stranding process that interlaced the coil with the braid matrix, a length of the braid matrix being melted such that the plurality of polymer fibers are coalesced together along the length, and a length of the coil being embedded in the melted braid matrix, wherein the proximal length includes a proximal segment and a distal segment, wherein the melted length of the braid matrix extends only along the distal segment of the proximal length; and an extruded polymer layer overlaying the tubular wall.

9. The body of claim 8, wherein the distal segment extends adjacent to the distal-most length.

10. The body of claim 9, further comprising a polymer liner extending along all or a portion of the proximal length contacting an inner circumference of the tubular wall, the braid matrix and coil extending around the liner, and the proximal segment extending proximally from the distal segment.

11. The body of claim 10, wherein the polymer liner extends only along the proximal segment of the proximal length, and the polymer liner comprises a multi-lumen tube.

12. The body of claim 11, wherein the distal-most length includes an internal shoulder, and a distal end of the coil extends around the shoulder; and the liner includes a lumen to accommodate a pull wire of the catheter so that a distal end of the pull wire can be coupled to the shoulder of the distal-most length.

13. The body of claim 12, wherein the distal-most length defines a receptacle for an implantable medical device, the distal-most length being terminated by an opening into the receptacle, the opening being sized to allow passage of the medical device therethrough.

14. The body of claim 8, wherein the distal-most length defines a receptacle for an implantable medical device, the distal-most length being terminated by an opening into the receptacle, the opening being sized to allow passage of the medical device therethrough.

* * * * *